(12) United States Patent
Cabiri et al.

(10) Patent No.: US 10,828,421 B2
(45) Date of Patent: Nov. 10, 2020

(54) INJECTOR DEVICE WITH FLOW PATH AND DRIVE

(71) Applicant: West Pharma. Services IL, Ltd., Ra'anana (IL)

(72) Inventors: Oz Cabiri, Hod Hasharon (IL); Paul H. Norton, St. Augustine, FL (US); Ran Hezkiahu, Herzliya (IL)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 342 days.

(21) Appl. No.: 15/766,844

(22) PCT Filed: Oct. 10, 2016

(86) PCT No.: PCT/US2016/056233
§ 371 (c)(1),
(2) Date: Apr. 9, 2018

(87) PCT Pub. No.: WO2017/062938
PCT Pub. Date: Apr. 13, 2017

(65) Prior Publication Data
US 2019/0060572 A1 Feb. 28, 2019

Related U.S. Application Data

(63) Continuation of application No. 15/204,542, filed on Jul. 7, 2016, now Pat. No. 10,576,207, and a (Continued)

(51) Int. Cl.
*A61M 5/28* (2006.01)
*A61M 5/31* (2006.01)
(Continued)

(52) U.S. Cl.
CPC ............ *A61M 5/28* (2013.01); *A61M 5/3134* (2013.01); *A61M 5/3202* (2013.01);
(Continued)

(58) Field of Classification Search
CPC .... A61M 5/28; A61M 5/3134; A61M 5/3202; A61M 5/3204; A61M 5/14248; A61M 5/1456
See application file for complete search history.

(56) References Cited

U.S. PATENT DOCUMENTS

| | | | |
|---|---|---|---|
| 1,125,887 A | 1/1915 | Schimmel | |
| 1,321,550 A | 11/1919 | Platt | |
| 4,710,178 A | 12/1987 | Henri et al. | |
| 5,275,582 A | 1/1994 | Wimmer | |
| 5,478,316 A * | 12/1995 | Bitdinger | ............ A61M 5/2033 604/135 |
| 5,858,001 A * | 1/1999 | Tsals | .................. A61M 5/14248 604/135 |

(Continued)

FOREIGN PATENT DOCUMENTS

| DE | 855313 C | 11/1952 |
|---|---|---|
| EP | 2364739 A1 | 9/2011 |

(Continued)

OTHER PUBLICATIONS

Int'l Search Report and Written Opinion dated Dec. 5, 2016 in Int'l Application No. PCT/US2016/056233.

*Primary Examiner* — Jason E Flick
*Assistant Examiner* — Tasnim Mehjabin Ahmed
(74) *Attorney, Agent, or Firm* — Panitch Schwarze Belisario & Nadel LLP

(57) ABSTRACT

A device for drug injection has a cartridge, which in turn has a reservoir and a fluid path. The fluid path carries a fluid for injection from the reservoir to the place where the patient is to be injected. The fluid path comprises a needle, and the fluid path is kept sterile. A drive chain extends the needle to the injection point, but is only mechanically connected to the fluid path to operate the needle, the mechanical connection being such as to operate the needle while maintaining the fluid path sterility.

14 Claims, 14 Drawing Sheets

Related U.S. Application Data continuation of application No. 15/269,248, filed on Sep. 19, 2016, now Pat. No. 10,086,145, which is a continuation-in-part of application No. 14/861,478, filed on Sep. 22, 2015, now Pat. No. 9,987,432.

(60) Provisional application No. 62/284,806, filed on Oct. 9, 2015, provisional application No. 62/281,536, filed on Jan. 21, 2016.

(51) Int. Cl.

| | | |
|---|---|---|
| *A61M 5/142* | (2006.01) | |
| *A61M 5/32* | (2006.01) | |
| *A61M 5/34* | (2006.01) | |
| *B65D 1/36* | (2006.01) | |
| *B65D 25/10* | (2006.01) | |
| *B65D 5/50* | (2006.01) | |
| *B65D 21/02* | (2006.01) | |
| *A61M 5/158* | (2006.01) | |
| *A61M 5/145* | (2006.01) | |

(52) U.S. Cl.
CPC ............ *A61M 5/3204* (2013.01); *A61M 5/34* (2013.01); *B65D 1/36* (2013.01); *B65D 5/503* (2013.01); *B65D 21/0233* (2013.01); *B65D 25/108* (2013.01); *A61M 5/1456* (2013.01); *A61M 5/14248* (2013.01); *A61M 2005/1581* (2013.01); *A61M 2005/312* (2013.01); *A61M 2005/341* (2013.01); *A61M 2205/3306* (2013.01); *A61M 2207/00* (2013.01)

(56) References Cited

U.S. PATENT DOCUMENTS

| | | |
|---|---|---|
| 6,189,292 B1 | 2/2001 | Odell et al. |
| 6,500,150 B1 | 12/2002 | Gross et al. |
| 6,719,141 B2 | 4/2004 | Heinz et al. |
| 6,824,529 B2 | 11/2004 | Gross et al. |
| 6,843,782 B2 | 1/2005 | Gross et al. |
| 7,967,795 B1 | 6/2011 | Cabiri |
| 8,496,862 B2 | 7/2013 | Zelkovich et al. |
| 8,603,028 B2 | 12/2013 | Mudd et al. |
| 8,721,603 B2 | 5/2014 | Lundquist |
| 2005/0154353 A1 | 7/2005 | Alheidt |
| 2009/0093792 A1 | 4/2009 | Gross et al. |
| 2013/0131589 A1 | 5/2013 | Mudd et al. |
| 2013/0253434 A1 | 9/2013 | Cabiri |
| 2014/0163526 A1 | 6/2014 | Cabiri et al. |
| 2014/0243786 A1* | 8/2014 | Gilbert .............. A61M 5/14248 604/506 |
| 2015/0112278 A1 | 4/2015 | Ray et al. |
| 2015/0157806 A1 | 6/2015 | Knutsson |
| 2016/0354553 A1* | 12/2016 | Anderson ........... A61M 5/3287 |

FOREIGN PATENT DOCUMENTS

| | | |
|---|---|---|
| EP | 2452708 A1 | 5/2012 |
| WO | 9721457 A1 | 6/1997 |
| WO | 2005070485 A1 | 8/2005 |
| WO | 2009043000 A1 | 4/2009 |
| WO | 2013036602 A1 | 3/2013 |
| WO | 2016087626 A1 | 6/2016 |
| WO | 2016087627 A1 | 6/2016 |

\* cited by examiner

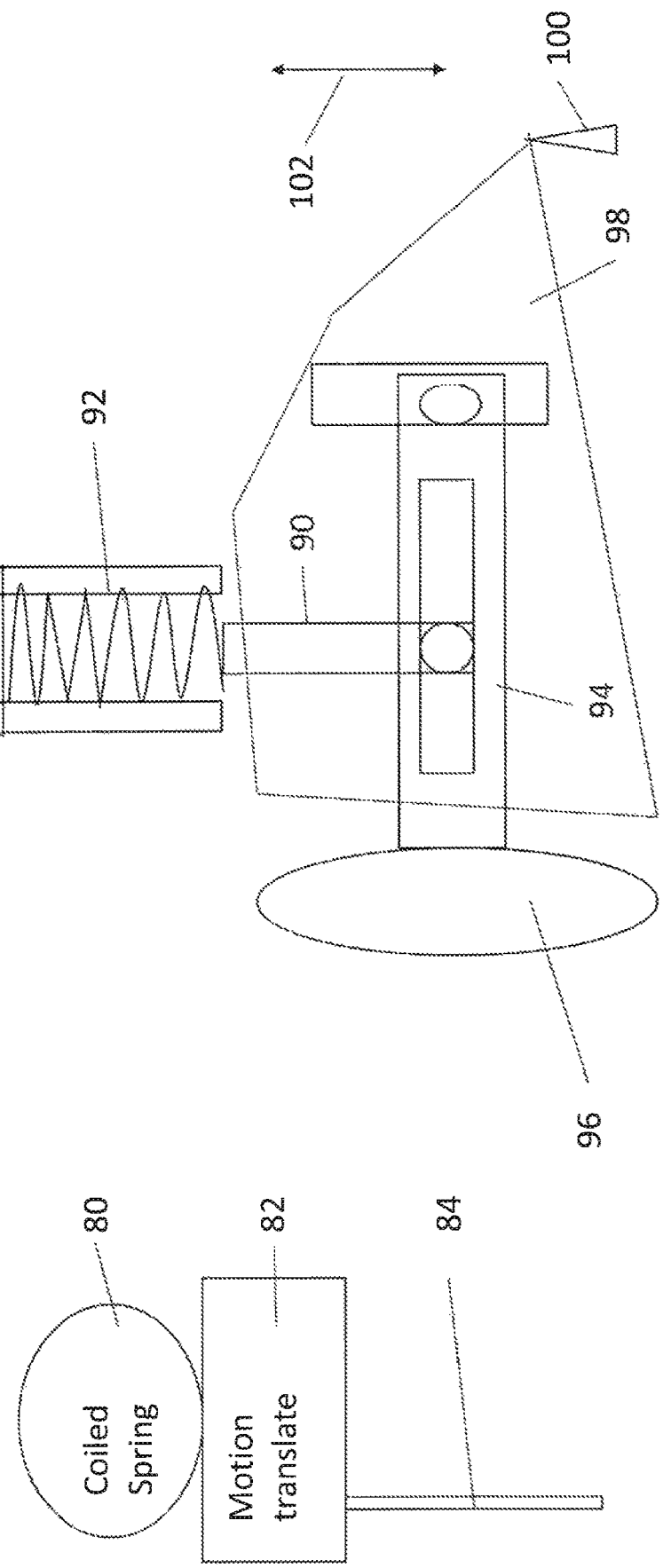

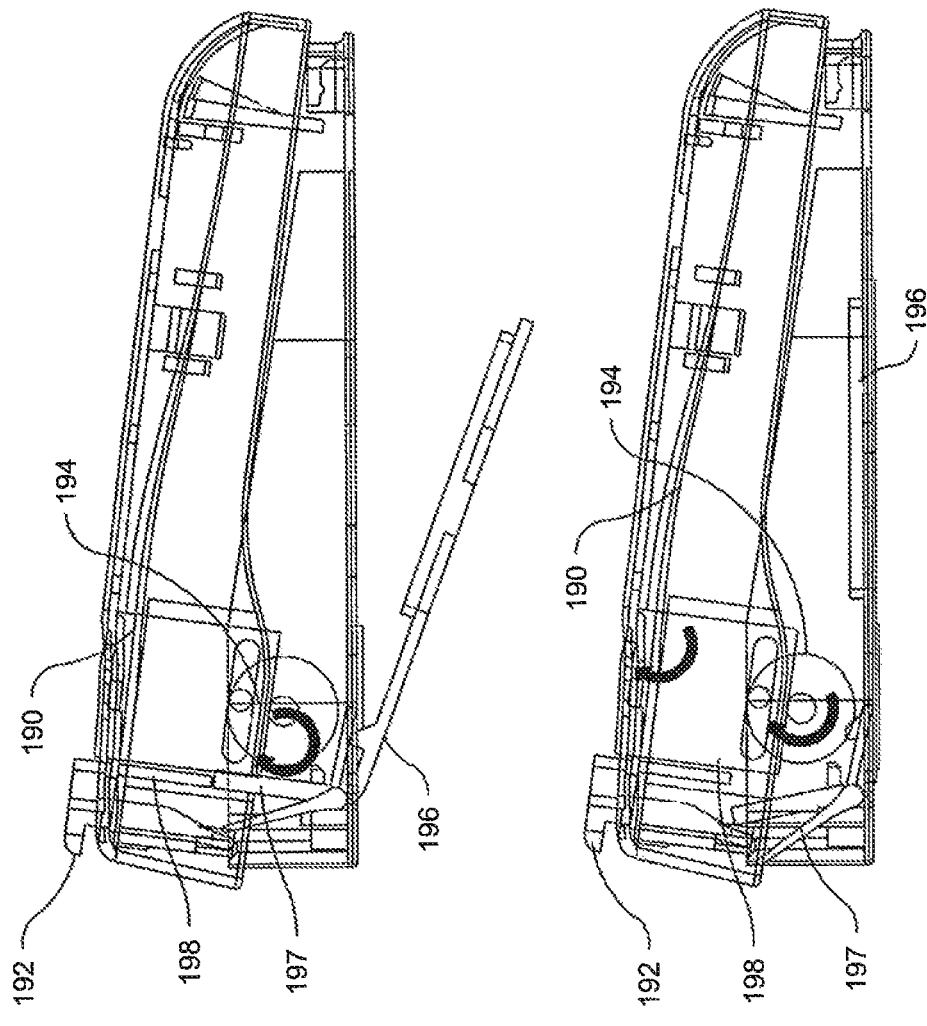

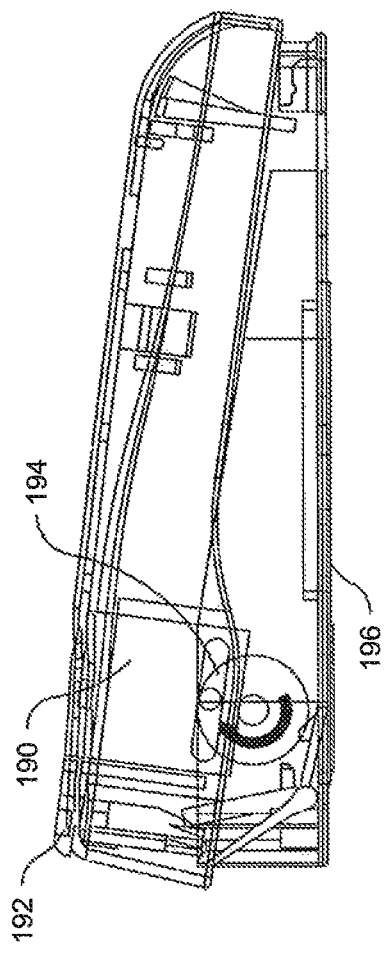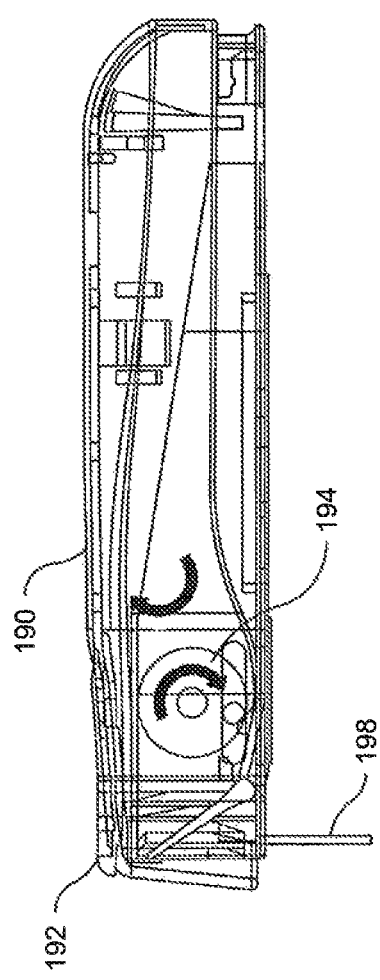

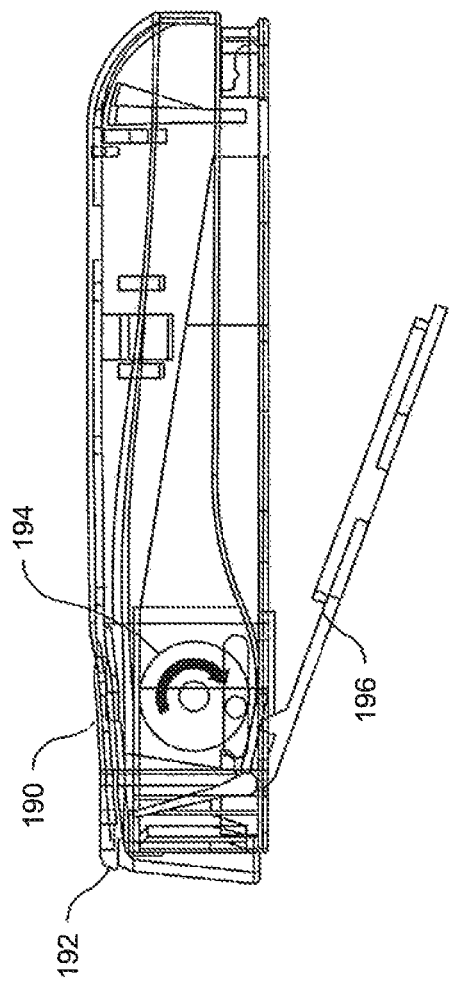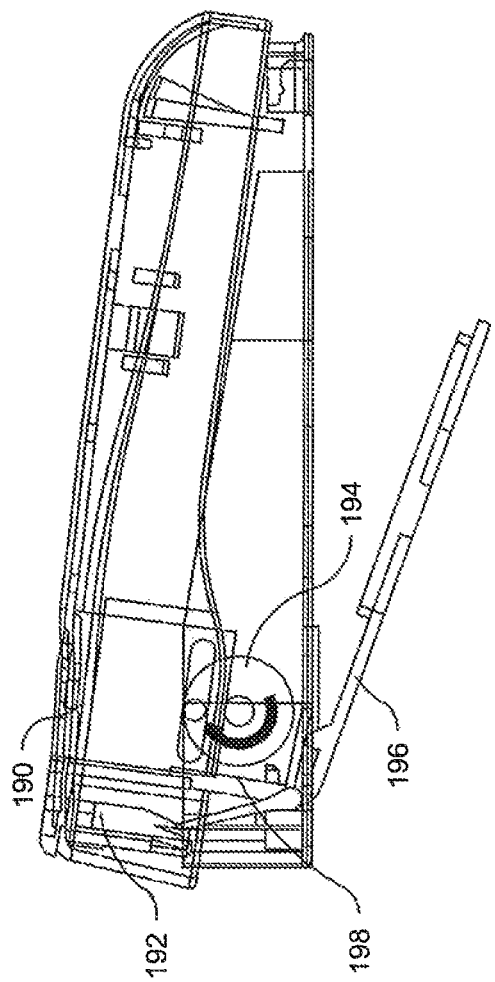

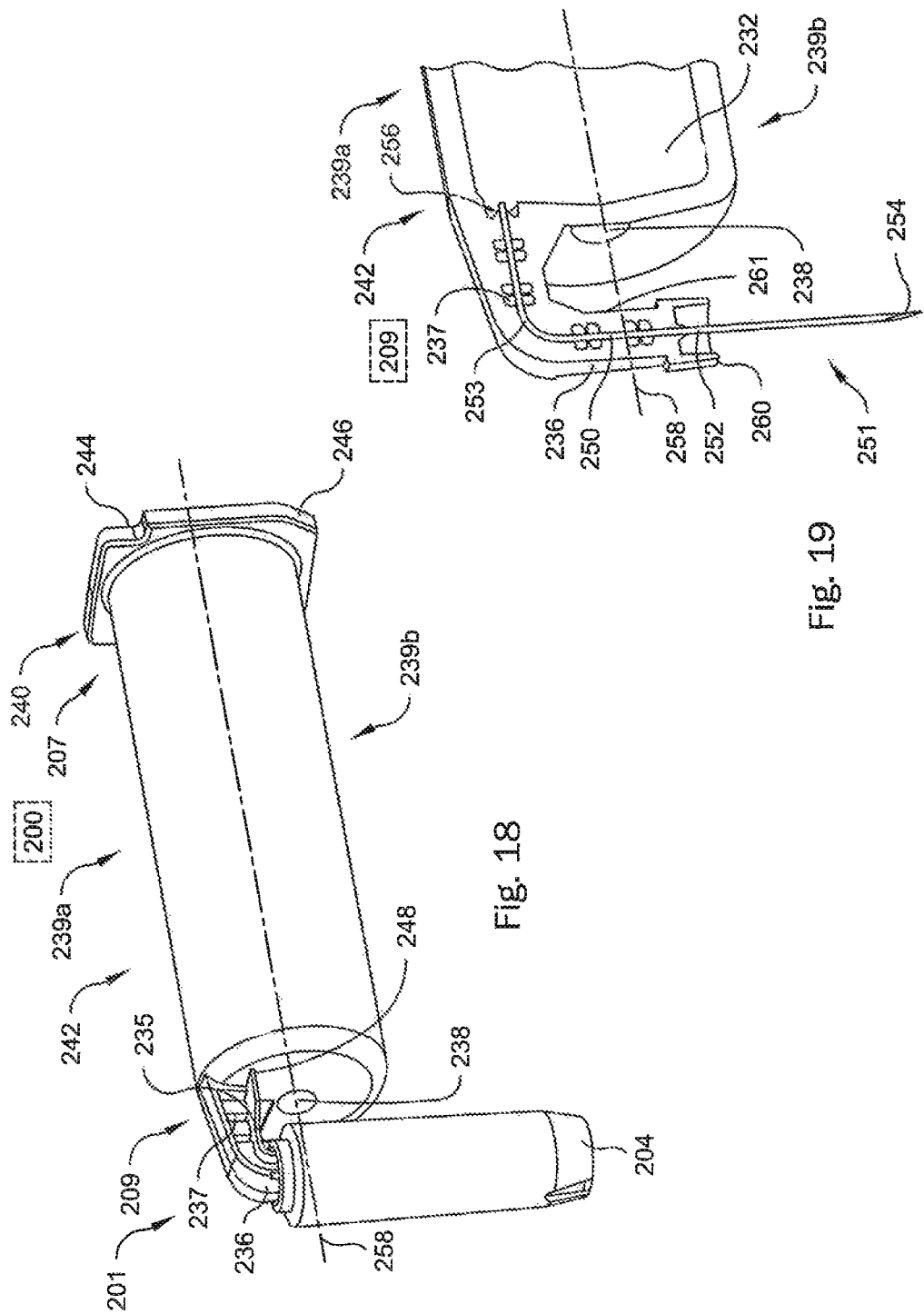

INJECTOR DEVICE WITH FLOW PATH AND DRIVE

FIELD AND BACKGROUND OF THE INVENTION

The present invention, in some embodiments thereof, relates to an injector device with a flow path for the material to be injected and a drive mechanism for extending and retracting the needle, and, more particularly, but not exclusively, to an arrangement for ensuring the sterility of the flow path.

U.S. Pat. No. 6,843,782 to Joseph Gross et al, assigned to Elan Pharma International Limited, discloses an injector device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend which directs the tip of the needle substantially perpendicular to the skin-contacting surface. In use, the tip of the needle is adapted to penetrate the skin of the subject.

In the cited device, the fluid path extends from the syringe to the needle and is connected to the needle in a straight line and is in this state when the device is inserted into the filler device for loading with the material to be injected. The needle remains straight and is covered by the needle cap as it is removed from the filling device. Subsequently, the needle is bent while filled with fluid, and bending the needle is irreversible.

Therefore if the cited device is disassembled and the cartridge/fluid path removed, it cannot be returned to the original state at which it was immediately after filling. Thus if the injection material expires or the device needs to be recalled, say if a batch is found to have been contaminated, the device cannot be emptied and refilled for use.

A further disadvantage of the cited device is that bending the needle while the cartridge is full causes metallic particles from the needle to be released into the injection material. This would not be inspected during the conventional particle test in the existing automatic filling process. The metallic particles compromise the purity of the injection material and thus such a device cannot be obtain approval for use.

SUMMARY OF THE INVENTION

The present embodiments provide a fluid path in which the needle is bent prior to filling. The integrity of the fluid path is retained with the cartridge or reservoir and as long as the injector has not been used, the cartridge can be exchanged. A removable cover may be provided to facilitate such removal.

The present embodiments ensure a sterile fluid path which is separate from the needle drive mechanism. In embodiments the drive mechanism is not itself sterile. Thus if there is a fault with the drive mechanism, the fluid path can be extracted as a whole and placed in a different device, or in some cases the drive mechanism can be fixed, without compromising the sterility of the fluid path.

The connection between the fluid path and the drive mechanism may be purely mechanical. One of the consequences is that the mechanical parts and the biologically active fluid parts can be separated for more environmentally friendly disposal.

The fluid path is sterile while the drive mechanism and the rest of the device may not be. Thus there is no compromise of the sterility of the injection when the injector device is placed directly on the patient's skin for injection.

The present embodiments may allow for easy handling. In particular a patient who is self-injecting usually places the device on one of his or her arms. In such a case there is only one hand available to operate the device. In the present embodiments, once the device is gripped in one hand, it is possible to remove the needle shield and adhesive with one motion from the front to back and there is no need to change the holding position on the device, which would require a second hand.

The device may be designed like a computer mouse to be gripped by the fingers of a single hand and, like a computer mouse, the gripping fingers are in the right place to activate the needle. Removal of the device is also possible in a single peeling motion from front to back or from back to front.

According to an aspect of some embodiments of the present invention there is provided a device for drug injection comprising:

a cartridge, the cartridge having a lengthwise axis and being movably mounted in the device to rotate or linearly displace the lengthwise axis, and comprising a reservoir and a fluid path, the fluid path for carrying a fluid for injection from a reservoir to a patient at an injection point, the fluid path comprising a needle, the needle being at a finite angle to the axis, the fluid path being sealed for sterility;

a drive chain for moving the cartridge, by the rotating or linearly displacing, to extend the needle to the injection point, the drive chain being mechanically connected to the fluid path to move the cartridge, the mechanical connection being such as to carry out the rotating or linearly displacing while maintaining the fluid path sterility. The embodiments illustrated herein show the cartridge being rotated but it can equally well be mounted to slide towards the base.

In an embodiment, the fluid path is preshaped to contain the angle, which may for example be a right angle.

In an embodiment, the mechanical connection is designed to allow the drive chain to be separated from the fluid path while maintaining the fluid path sterility.

An embodiment may comprise a housing and a button to operate the drive chain, the housing being shaped and sized to be held in a one handed grip, the button being positioned to be operated by fingers of the one-handed grip.

An embodiment may comprise a front end and a rear end and an adhesive layer for attachment to skin of the patient for the injection.

The device may be attachable and detachable to the patient via the adhesive layer using the one-handed grip and a rolling motion between the front end and the rear end.

An embodiment may comprise a cover in the housing, the cover being removable to allow removal of the reservoir via the housing.

In an embodiment, the reservoir is removable with the fluid path.

According to a second aspect of the present invention there is provided a method for filling, loading and removing a cartridge in an injector device wherein the cartridge is held lengthwise at an angle to a plane of the skin of a patient receiving an injection, the method comprising:

obtaining a cartridge, the cartridge attached to a fluid path for carrying fluid from the cartridge to an injection site;

adding an angle to the fluid path so that the fluid path exits the cartridge in a lengthwise axis of the cartridge and is delivered to the patient perpendicularly to the plane;

after adding the angle, filling the cartridge with injection fluid;

loading the cartridge, with the fluid path, into the injector device; and removing the cartridge, with the fluid path, from the injector device.

An embodiment may comprise carrying out the removing upon noticing a fault in the injector device, and placing the cartridge in a second injector device.

An embodiment may comprise carrying out the removing upon noticing a fault in the reservoir, and placing another cartridge in the injector device.

An embodiment may comprise providing a housing for the injector device and a removable cover in the housing and opening the removable cover to carry out the loading and the removing.

In an embodiment, the loading the cartridge comprises placing the fluid path in mechanical connection with a drive mechanism, the drive mechanism being to extend a needle of the fluid path to an injection site on the patient.

In an embodiment, the fluid path is sterile, the method comprising applying and removing the mechanical connection while retaining the fluid path sterility.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 4 is a simplified block diagram showing elements of the needle drive chain of the device of FIG. 1;

FIGS. 5-11 are simplified diagrams showing needle drive chains in different implementations of the elements of FIG. 4;

FIGS. 12-17 are simplified diagrams showing different stages in the injection process using the device of FIG. 2 and showing different states of the drive chain;

FIG. 18 is a simplified diagram illustrating the cartridge of FIG. 2 with a bent fluid path;

FIG. 19 is a cutaway view of the fluid path of FIG. 18;

DESCRIPTION OF SPECIFIC EMBODIMENTS OF THE INVENTION

Figure 1:
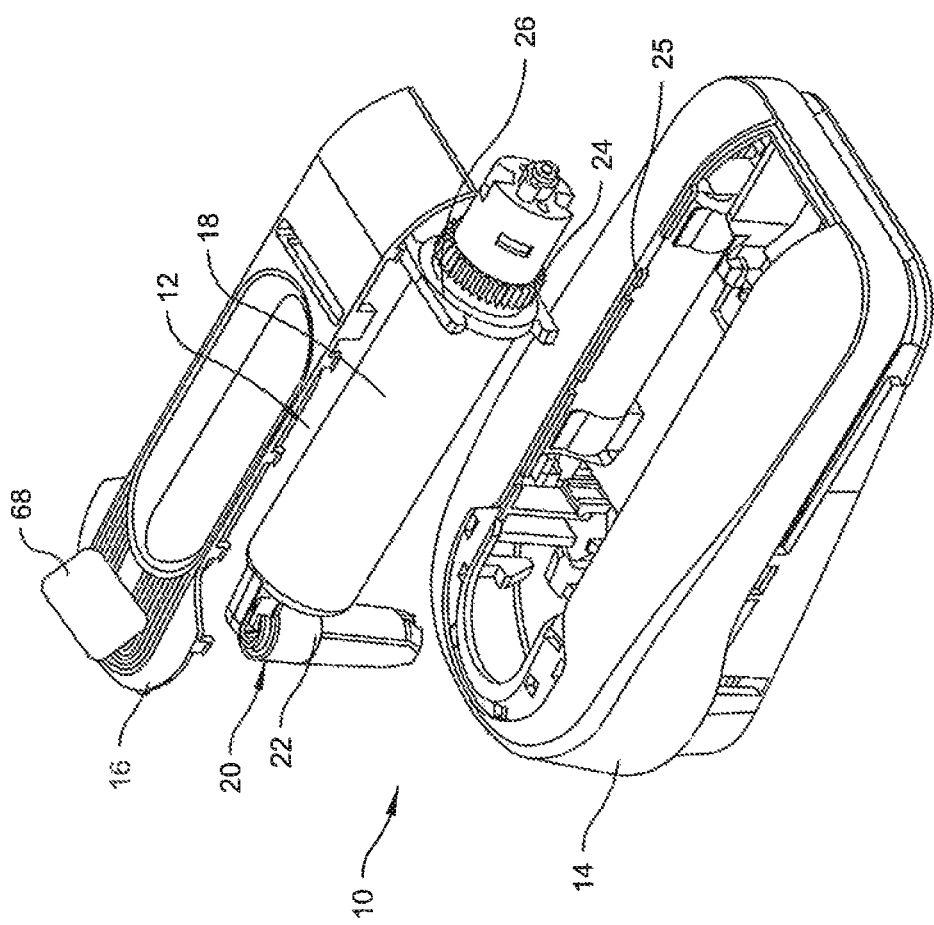
FIG. 1 is a simplified diagram showing a button operated injector device, a cartridge and a removable cover according to an embodiment of the present invention.

The present invention, in some embodiments thereof, relates to an injector device with a flow path for the material to be injected and a drive mechanism for extending and retracting the needle, and, more particularly, but not exclusively, to an arrangement for ensuring the sterility of the flow path.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 illustrates a device 10 for drug injection. Device 10 includes a cartridge 12, a housing 14 that covers the device from the outside and a removable cover 16 which fits onto the housing 14. The cover 12 may be removed to give access to the cartridge, for either insertion or removal.

The cartridge 12 has a barrel reservoir 18 for holding the fluid to be injected and a fluid path 20 for carrying the fluid from the reservoir 18 to the point of injection. The fluid path comprises a needle, not shown in this figure, under a needle cover 22. The fluid path is kept sterile by being sealed from the device, and the only contacts with the device are mechanical contacts which act through the seal without compromising the integrity of the seal and thus of the sterility. Thus the device 10 as a whole need not be sterile. As a result the cartridge can be inserted and removed without compromising its sterility.

Cog 24 is engaged by a mechanism, typically an electric motor to push a plunger within the bagel to carry out the injection. Engagement frame 26 on the cartridge engages a holding recess 25 within the device to position the cartridge correctly.

Figure 2:
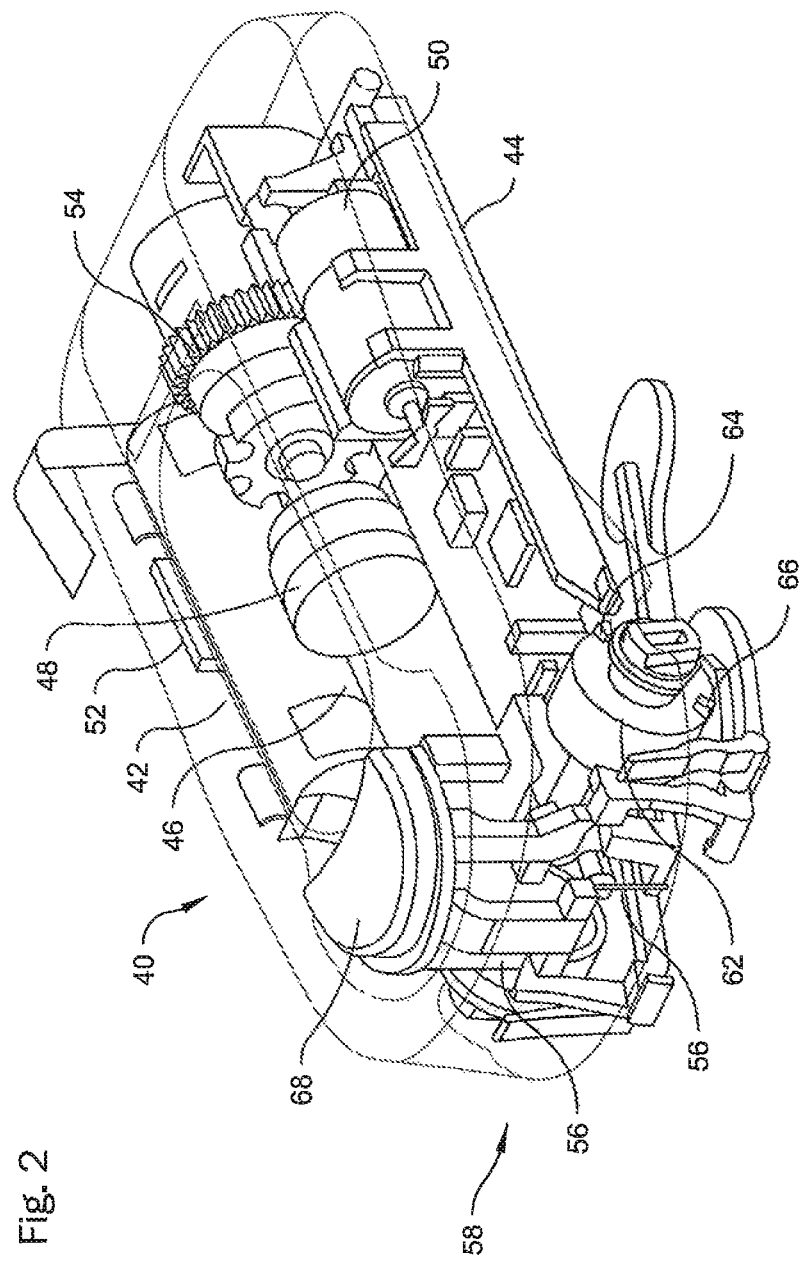
FIG. 2 is a simplified diagram showing an upper perspective view of the injector device of FIG. 1 with the cover and barrel rendered transparent.

Reference is now made to FIG. 2 which is a simplified diagram showing a version 40 of the device of FIG. 1 in which a drive chain extends the needle to the injection point. That is to say, the device is placed on the user's skin with the needle retracted and a drive chain is activated to push the needle downwards under the skin of the user. The upper part of the housing and of the cartridge are made transparent to show the parts of the drive chain.

The drive chain is mechanically connected to the fluid path to operate the needle. The mechanical connection simply pushes on the fluid path from the outside and does not compromise the sterility within the fluid path. The mechanical connection thus operates the needle while maintaining the fluid path sterility.

One non-limiting embodiment of the drive chain is now described with reference to FIG. 2. The embodiment of FIG. 2 is based on a wound spring, although embodiments based on other sources of tension, on electric motors, on pressing by the user, and on other mechanisms may also be used. The drug delivery device includes upper and lower longitudinal surfaces 42 and 44, wherein lower longitudinal surface 44 is intended to be placed against the skin. Reservoir 46 contains a drug to be injected and plunger 48 empties the drug into the needle for injection. The plunger is operated by a plunger operation mechanism including a small electric motor 50 and battery 52, and a motion translation arrangement 54. A needle insertion mechanism 56 is located at a forward end 58 of the drug delivery device 40 to insert needle 60 into the skin of a patient and withdraw the needle afterwards.

A motion source may be provided to operate the needle 60. The motion source may in one embodiment be a tensioned wheel 62. In other embodiments a plunger may be pushed by a spring. The tensioned wheel may comprise two lugs 64 and 66 which interrupt the motion of the wheel.

A user-operated control for the motion source may comprise button 68. It is noted that the button may be a separate component that is compressible or it may be a flexible part of the housing that can be pressed. As the button is pressed once, the first lug 64 is released, allowing the wheel to rotate half a turn. The motion of the half turn is translated into an insertion motion for needle 60, thus inserting the needle. In an embodiment, the button 68 is a separate component from the device housing, so that the housing shields the button from accidental pressing. To reach the button, the cover part of the housing may be lowered, thus providing a two stage activation system and adding safety to the device.

The second lug 66 then serves as an interrupter, stopping motion of the wheel at a preset location at which the insertion motion of the needle is complete. The second lug thus divides the wheel motion into a first motion part and a second motion part, the two motion parts being in continuity with each other.

A second wheel may be provided on the other side of the button 68, not visible in the present figure, to provide more balanced motion.

As the wheel is released a second time, it rotates from the second lug to the first lug on the second part of a complete rotation, and the motion is translated into retraction of the needle.

In an alternative embodiment, the needle may not be retracted, but rather the base may extend to shield the needle when the device is removed from the skin.

Alternatively or additionally, the linear movement of the needle retraction may for example be by means of multiple actuators or springs moving the needle in opposite directions. In some embodiments, the activation button may return to the original position and/or be locked after injection.

Alternatively or additionally, needle retraction may be activated by a switch. For example there may be a needle retraction switch and/or after needle insertion the activation button may be reused as a needle retraction switch.

A motion translation mechanism to be discussed in greater detail below, connects the wheel or any other source of the continuous motion to the needle 60. The motion translation mechanism may insert the needle during the first motion part and may retract the needle during the second motion part.

In the case of a wheel as the motion source, the continuity of the motion is angular.

As will be discussed below, instead of or in addition to a wheel with lugs, a suitably shaped cam may be used.

Thus the device has a housing, and button 68 which operates the drive chain as will be described in greater detail below. The housing is shaped and sized to be held in a one handed grip, in the same way that a computer mouse is so designed. The button is positioned with the one-handed grip in mind to be operated by the fingers while in the one-handed grip.

The device may have an adhesive layer at the base for attachment to the skin of the patient so as to hold the device still for the duration of the injection. For certain injections there may be a need to inject slowly so the device needs to be in the same position for several minutes. Preferably, the device is attachable and detachable via the adhesive layer using the one-handed grip and a rolling motion between the front and back of the device. Thus the device is firmly positioned and adhered and then peeled off after use.

As mentioned, the cover 16 may be removable to allow loading and removal of the reservoir via the opening made in the housing.

The entire cartridge is removed, thus taking out the reservoir with the accompanying fluid path.

Figure 3:
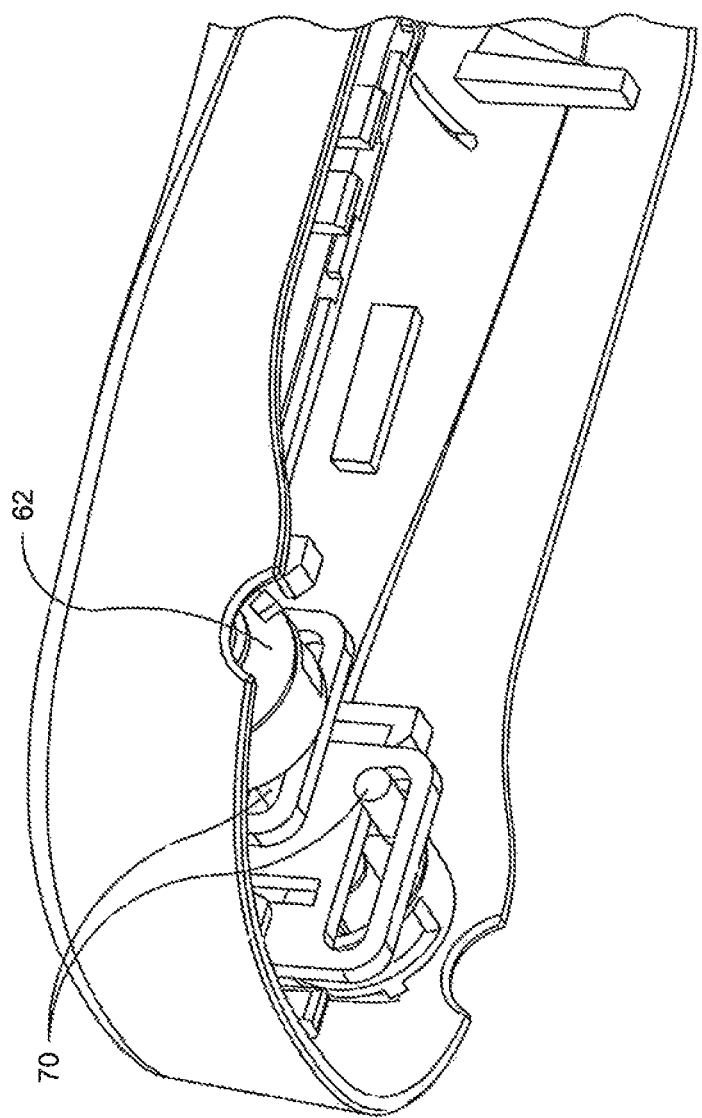
FIG. 3 is a perspective view from below showing the injector device of FIG. 1 with the base removed, and illustrating elements of the needle drive chain.

Reference is now made to FIG. 3, which is a simplified diagram showing how the wheels are connected to the cover of the device 40, via pin 70.

Lugs 62 and 64 are optional and may be omitted in some embodiments. However an element is required which is responsible to prevent the cover from being lowered prior to use. Such an element may be a contact between the button and the structure (base/cover) or the wheel lug 62, 64 or the pin 70. A second element or contact is responsible for preventing movement when the wheel is held in the lower or extended position. Again the feature may be provided by the contact between the safety latch lug and wheel pin, A third element/contact is responsible for arresting motion at the end of travel, thus ensuring that the needle, once retracted, cannot be extended again. Such a feature may be provided by contact between the wheel lug or wheel pin and the structure.

Reference is now made to FIG. 4, which is a simplified diagram showing an embodiment in which the motion source is a coiled spring 80 connected directly to a motion translation unit 82. The motion translation unit comprises a series of levers which translate the rotary uncoiling of the spring 80 into a lowering and a raising part motion of the needle 84. That is to say, as the spring uncoils, the motion is divided into two parts, one translating into a first direction and the other translating into a second opposite direction.

Reference is now made to FIG. 5. In FIG. 5 the motion source is a plunger 90 tensioned by coiled spring 92. The plunger is pushed linearly by coiled spring 92 and is pivotally attached to beam 94 which rotates around wheel 96. Beam 94 is pivotally attached to cam 98, which is in turn pivotally attached at pivot point 100, so that initial travel is downwards and subsequent travel is upwards. As the plunger is pushed by the coiled spring, the motion is divided into two parts, one translating into a first direction and the other translating into a second opposite direction, as indicated by arrow 102.

Figure 6:
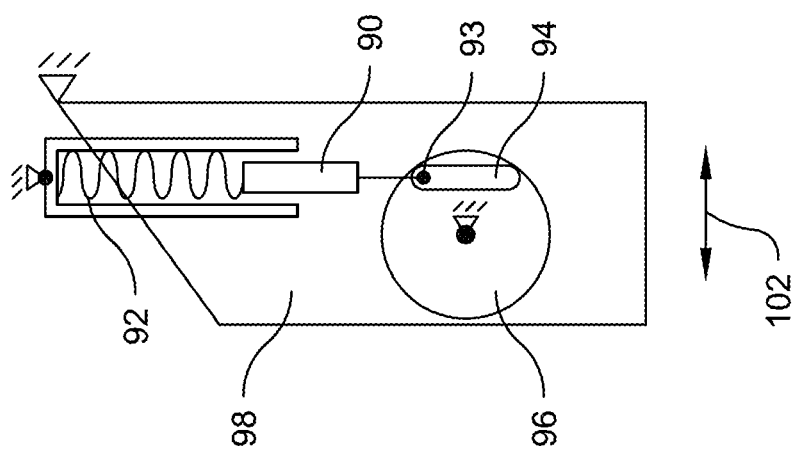

Reference is now made to FIG. 6 which is an alternative embodiment of a motion translation mechanism. Again the motion source is plunger 90 tensioned by coiled spring 92. The plunger is pushed linearly by coiled spring 92 and is pivotally attached at pivot 93 to beam 94, which rotates cam 98. Due to constraints of the fitting, the wheel is turned first one way and then the opposite way, as indicated by arrow 102.

Figure 7:
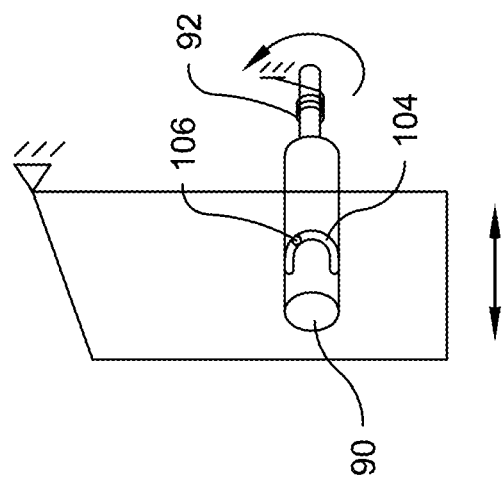

Reference is now made to FIG. 7, which is another alternative embodiment of a motion translation mechanism. Again the motion source is plunger 90 tensioned by coiled spring 92. The plunger is in this case rotated by coiled spring 92 and has shaped slit 104. Pin 106 rides in the slit—extending in the direction out of the paper and thus turning a wheel in a plane at 90 degrees to the image first in one direction and then in the other direction.

Figure 8:
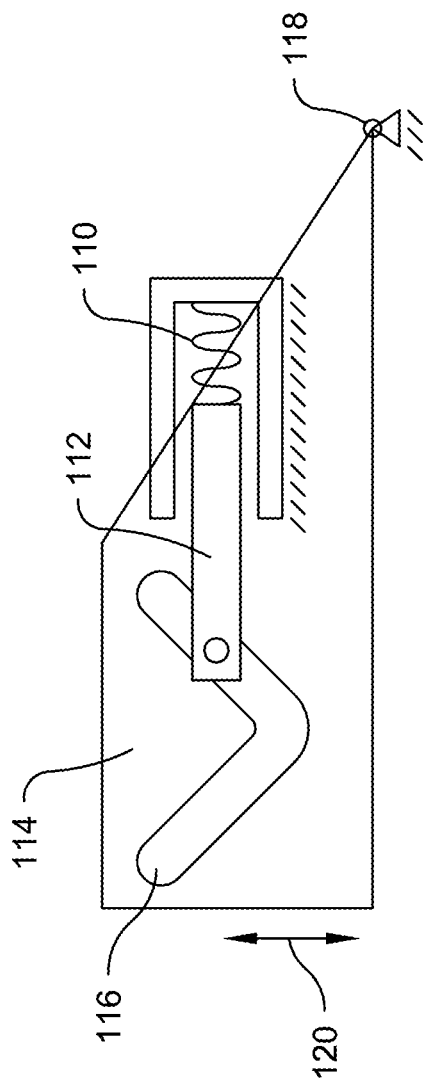

Reference is now made to FIG. 8 which illustrates a variation of FIG. 5 in which a coiled spring 110 operates a plunger 112 to slide pivoted cam 114 over angled beam 116. The cam 114 is pivoted at pivot point 118. As the plunger moves, the motion is divided into two parts, one translating into a first direction and the other translating into a second opposite direction, as indicated by arrow 120.

Figure 9:
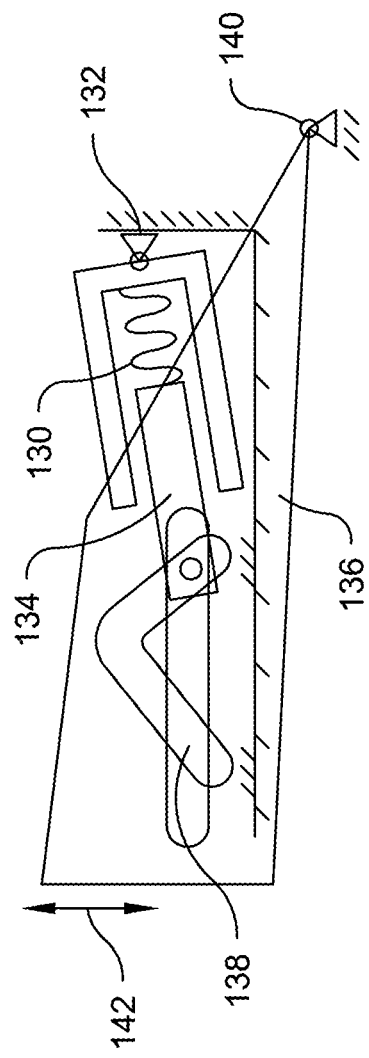

Reference is now made to FIG. 9, which is a simplified diagram illustrating a variation of the embodiment of FIG. 6. In FIG. 6 coiled spring 130 is itself pivoted at pivot point 132 and operates plunger 134 to push cam 136 against angled beam 138. The cam 136 is pivoted at pivot point 140. As the plunger is pushed, the motion is divided into two parts, one translating into a first direction and the other translating into a second opposite direction, as indicated by arrow 142.

Figure 10:
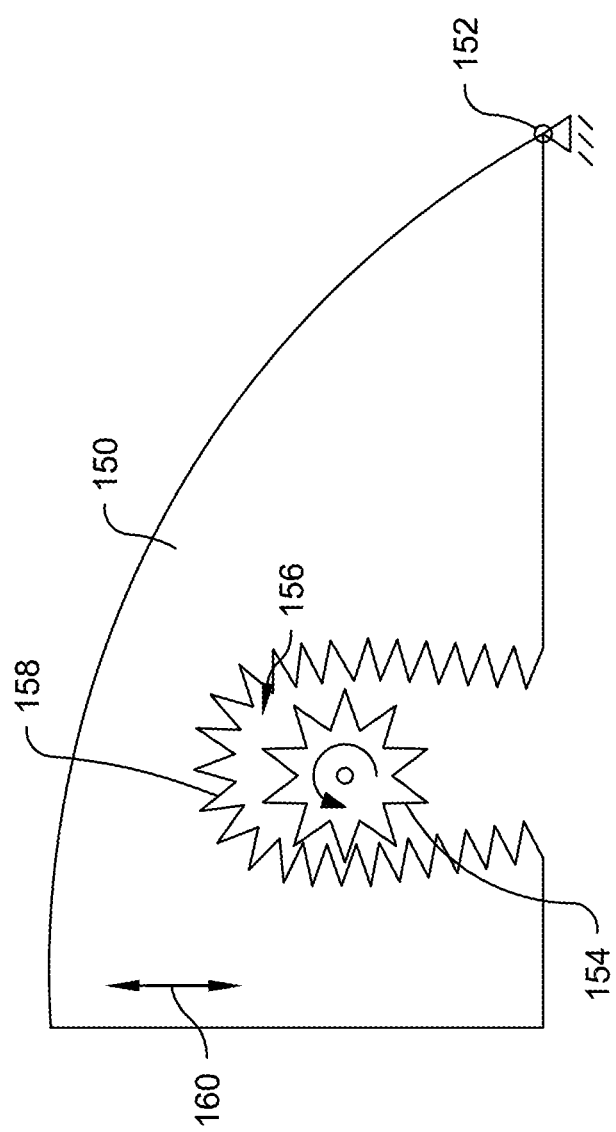

Reference is now made to FIG. 10, which illustrates a further variation of the present embodiments. In FIG. 10 a cam 150 is pivoted at pivot point 152 and a pre-tensioned cog wheel 154 lies inside the cam in a concave intrusion 156 with corresponding teeth 158. As the cog wheel 154 rotates, the motion is divided into two parts, one translating into a first direction and the other translating into a second opposite direction, as indicated by arrow 160.

Figure 11:
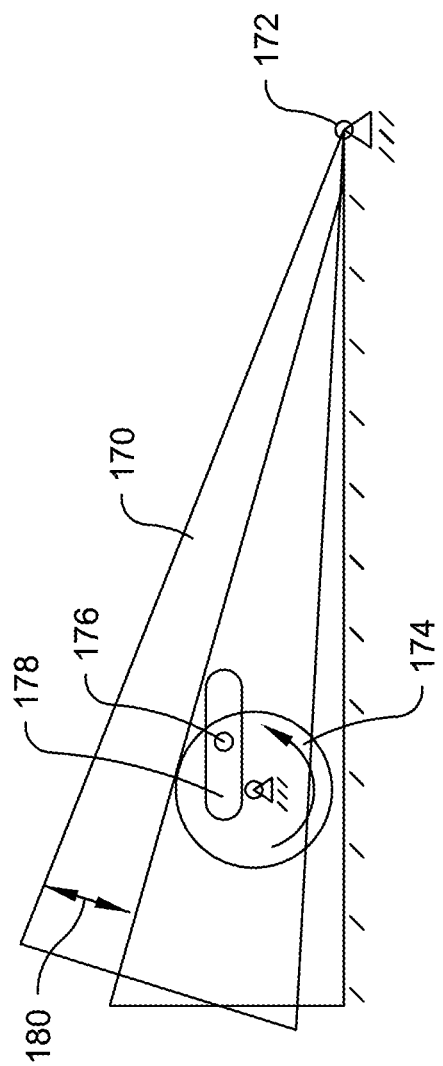

Reference is now made to FIG. 11, which is a simplified diagram illustrating a motion translation mechanism for the wheel embodiment of FIG. 2. Cam 170 is pivoted at pivot position 172. Wheel 174 is tensioned by a rotator and has a pivot 176 which moves in slot 178 within cam 170. The cam moves up and down as shown by arrow 180. The wheel is operated by the tensioned rotator which is typically a coiled spring, and the coiled spring unwinds to rotate the wheel about its axis.

Reference is now made to FIGS. 12 to 17, which are a series of diagrams showing successive stages of operation of the drive chain in the embodiment of FIG. 2. FIG. 12 is a simplified diagram showing an initial state of the device according to the present embodiments prior to use. The device has cover 190, user operable button 192, tensioned wheel 194, and safety latch 196. The device is loaded with drug prior to use and the button and cover are locked so that the button cannot be pressed and the cover cannot be depressed. Specifically the safety latch 196 may block pressing of the button due to arm 197 sitting under button extension 198.

Reference is now made to FIG. 13, which is a simplified diagram showing the device of FIG. 12 in a state just prior to use. Parts that are the same as in FIG. 9 are given the same reference numerals and are not described again except as needed for an understanding of the present figure. The device is placed against the skin on the injection site which pushes up the safety latch 196 against the base of the device, thus allowing the button to be pressed. The button is now possible to press because arm 197 has rotated forward and no longer sits under button extension 198. However the cover 190 is still locked although the button can now be pressed to release the needle.

The safety latch thus ensures that the button cannot be pressed unless the injector is placed flush against a flat surface. The safety latch mechanism is not restricted to the present embodiments but is suitable for any kind of injector which is placed flush against the patient's skin. More generally, the safety latch is a latching mechanism for preventing extension of the needle except in the presence of skin, and comprises a lever, namely safety latch 196, having an arm 197, the lever extending at a predetermined angle below the base of the drug delivery device to insert the arm to prevent motion of the user-operated control, namely button 192, to render the button inoperable. The lever is displaced from the predetermined angle shown in FIG. 9 as it is pressed flush against the base by the presence of skin, thereby moving the arm forward and releasing the button.

FIG. 14 is a simplified diagram showing the device of FIG. 12 with the button 192 being pressed to insert the needle. Parts that are the same as in FIG. 12 are given the same reference numerals and are not described again except as needed for an understanding of the present figure. The button 192 is pressed and wheel 194 is released to rotate under tension and insert the needle.

FIG. 15 is a simplified diagram showing the device of FIG. 12 after the needle has been inserted for injection. Parts that are the same as in FIG. 12 are given the same reference numerals and are not described again except as needed for an understanding of the present figure. The wheel 194 has rotated by half a rotation and needle 198 is extended from the device so that injection takes place.

FIG. 16 is a simplified diagram showing the device of FIG. 12 with the safety latch opened to release the wheel for retraction. Parts that are the same as in FIG. 12 are given the same reference numerals and are not described again except as needed for an understanding of the present figure. In FIG. 16, as the device is withdrawn from the skin after use, the safety catch 196 extends downwards, releasing tensioned wheel 194 for its second half turn. The half turn withdraws the needle. At the end of the half turn the wheel is arrested so that no further turning is possible.

FIG. 17 is a simplified diagram showing the device of FIG. 12 locked after use. Parts that are the same as in FIG. 12 are given the same reference numerals and are not described again except as needed for an understanding of the present figure. In FIG. 17 the cover 190 is raised, again locking the device so that used needle is not exposed.

In the above embodiment, the Base 196 acted as a mechanical proximity sensor. The Base 196 may be used by changing its angle relate to the body, to detect skin proximity and to release the wheel, or the interrupter on the wheel, to cause the second motion part on detecting of removal of the device from the user's skin. Thus the retraction of the needle occurs automatically upon removal of the device from the user. As above the proximity sensor is mechanical but an optical or infrared proximity sensor may also be used and electronically actuate the wheel release.

FIGS. 18 and 19 are perspective and cut away views of a syringe 200 which comprises a reservoir part or barrel 242 and a fluid path 201. The fluid path includes an angled extension 236 mounted on a bent arm off the center axis 258 of a cylindrical cavity 232 of a barrel 242 in accordance with an embodiment of the present invention. Optionally a fluid path connects to the cavity of the barrel and passes through the extension. Optionally the bent arm is molded and/or formed in one piece with barrel 242. For example extension 236 projects from a distal end 209 of barrel 242. Optionally the connection between extension 236 and barrel 242 is biased to the dorsal side 239a of barrel 242. In some embodiments a needle cap 204 is mounted on extension 236 at an approximately right angle to axis 258 of barrel 242. For example cap 204 faces towards the ventral side 239b of barrel 242. In some embodiments, a flange 240 may be supplied on the proximal end 207 of syringe 200. For example, flange 240 may be used to hang barrel 242 from a support tray of an automatic filling machine.

In some embodiments syringe 200 may include asymmetric features. For example, the fluid path may be connected non-centrically to the distal end of barrel 242. For example extension 236 projects from a distal end 209 of barrel 242. Optionally the connection between extension 236 and barrel 242 is biased to the dorsal side 239a of barrel 242. In some embodiments a needle cap 204 is mounted on extension 236 at an approximately right angle to axis 258. For example cap 204 faces towards the ventral side 239b of barrel 242. Optionally extension 236 and/or the mount for cap 204 is set back from a ventral side 239b of barrel 242. For example setting back extension 236 and/or the mount for cap 204 may facilitate designing a device with a lower profile (for example because the length of the mounting does not add to the profile of the device). Optionally syringe 200 may include a tab 248 and/or an indentation 238 and/or a protuberance and/or a cut out 244 and/or a beveled part 246 to facilitate attachment of syringe 200 to the drug delivery device.

In some embodiments an indentation and/or an indentation and/or a protuberance may be used to position syringe 200 and/or a cartridge in a delivery device. For example indentation 238 is conical and may interact with a protuberance and/or indentation in the delivery device to position the distal end 209 of the cartridge into alignment with the delivery device. For example an indentation and/or protuberance could include a pin and/or a matching hole. A bevel 246 and and/or cutout 244 and/or tab 248 may optionally interact with a complementary part in a delivery device.

In some embodiments a fluid path 250 connecting between cavity 232 of barrel 242 and extension 236 may pass through and/or be molded into syringe 200. Optionally (for example as illustrated in FIG. 19), a metal needle 252 forms a portion of fluid path 250. Optionally dead space in fluid path 250 is reduced by having the entire path inside needle 252, thus avoiding any issue of dead space in the plastic mold. For example an embedded portion 253 of needle 252 forms a bent fluid path 250 to a protruding portion 251. Protruding portion 251 optionally protrudes straight out of extension 236 at substantially a right angle to axis 258 of the cavity and/or axis 232 of barrel 242. The protruding end of needle 252 is optionally beveled and/or sharpened to facilitate insertion through the skin of a subject, as discussed hereinabove.

In some embodiments, a beveled needle tip 254 is oriented to avoid obstruction of needle 252, as discussed above. For example, the opening of beveled needle tip 254 is directed distally. In the case where needle tip 254 is inserted into a subject by pivoting around the proximal end of the syringe and/or tends to plow proximally as it is inserted into the subject, facing the opening distally may prevent needle obstruction.

In some embodiments an extension may have a non-uniform cross section. For example in the center section of extension 236 windows or holding channels 237 are formed. Optionally holding channels 237 are formed around needle supports that hold the needle during the molding process and are subsequently removed. Optionally the reservoir end of needle 252 may be supported by a core pin. For example, a space 256 left by the core pin in the molded syringe can be seen in FIG. 18. During molding, the core pin optionally blocks the hollow portion of needle 252 for example preventing the needle from being obstructed by the molded material.

In some embodiments, the size of the core pin holding the end of needle 252 in cavity 232 is made small to reduce the dead space 256 left over after molding. For example a core pin may have a concave and/or conical inner face that grasps the end of needle 252. Alternatively or additionally, a core pin may have a convex and/or conical face that fits into the hollow of needle 252. For example a core pin may include an inner convex portion that fits into the needle 252 and/or an outer concave portion that positions needle 252. Before molding, the outer concave portion of the core pin may position needle 252 in order to insert the inner convex portion of the core pin into the hollow of needle 252. Then the outer concave portion may be retracted before molding. Optionally during molding only the inner portion of the core pin remains in the mold. After molding the inner core pin is optionally removed leaving a reduced dead space when a drug is discharged from the syringe.

In some embodiments, extension 236 has an I-beam cross section as explained. Optionally ribs 235 are offset from the fluid pathway. For example the offset is sufficient to leave space for channels 237 around fluid path 250 and/or between ribs 235.

In some embodiments the end of extension 236 includes a mount for needle cap 204. For example the mount may include a sealing ring 260 and/or a tapered section 261. For example, sealing ring 260 may seal against the inside of cap 204. In some embodiments this may isolate protruding section 251 of needle 252 and/or protect it from contamination. For example, tapered portion 261 may be formed in ribs 235. In some embodiments, tapered section 261 may hold cap 204 rigidly to extension 236. Cap 204 may optionally be connected and/or disconnected from extension 236 by pulling and/or pushing cap 204 along the axis of extension 236 and/or along the axis of protruding section 251 of needle 252.

Thus, as shown, the fluid path may contain an angle. The mechanical connection is designed to allow the drive chain to be separated from said fluid path while maintaining said fluid path sterility.

Figure 20:
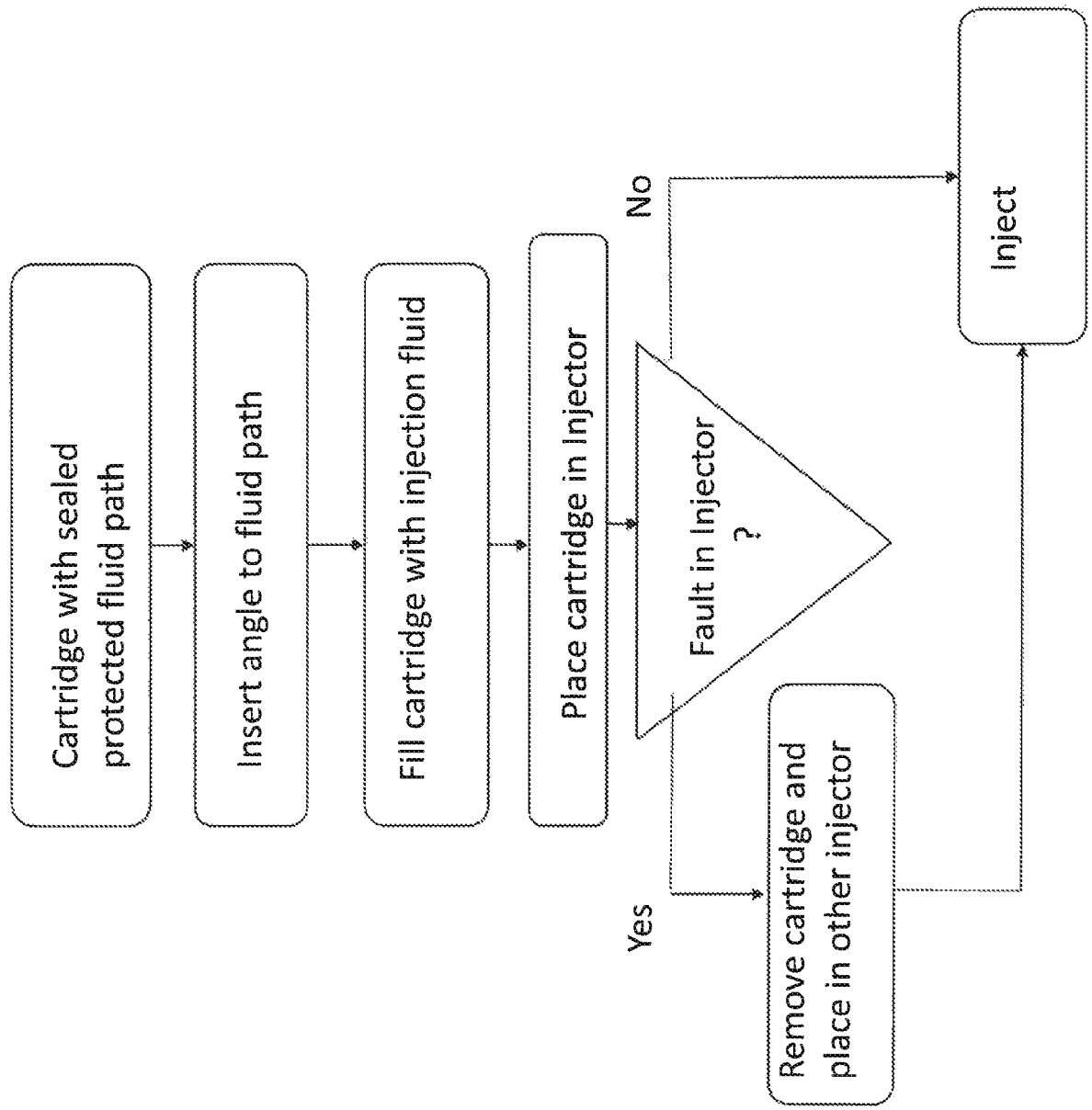
FIG. 20 is a flow chart showing a cartridge filling and replacing procedure according to one embodiment of the present invention.

Reference is now made to FIG. 20, which illustrates a method of filling, loading and exchanging a cartridge in accordance with embodiments of the present invention. As discussed, the cartridge is held lengthwise at an angle to the plane of the skin of the patient receiving the injection. In the method, the cartridge with the fluid path is obtained 300 and an angle is made in the fluid path, 302. With the angle in the fluid path the cartridge is filled 304 with injection fluid. Then the cartridge, now sealed to retain sterility, is placed in the injector device 306 and if all goes well and there is no fault 308 then the injector is used by the patient to carry out the injection 310. However if there is a fault in the injector device then the cartridge may be removed 312 and inserted into another injector device. Such a procedure is useful where the cost of the injection fluid is much higher than the cost of the injector device.

Figure 21:
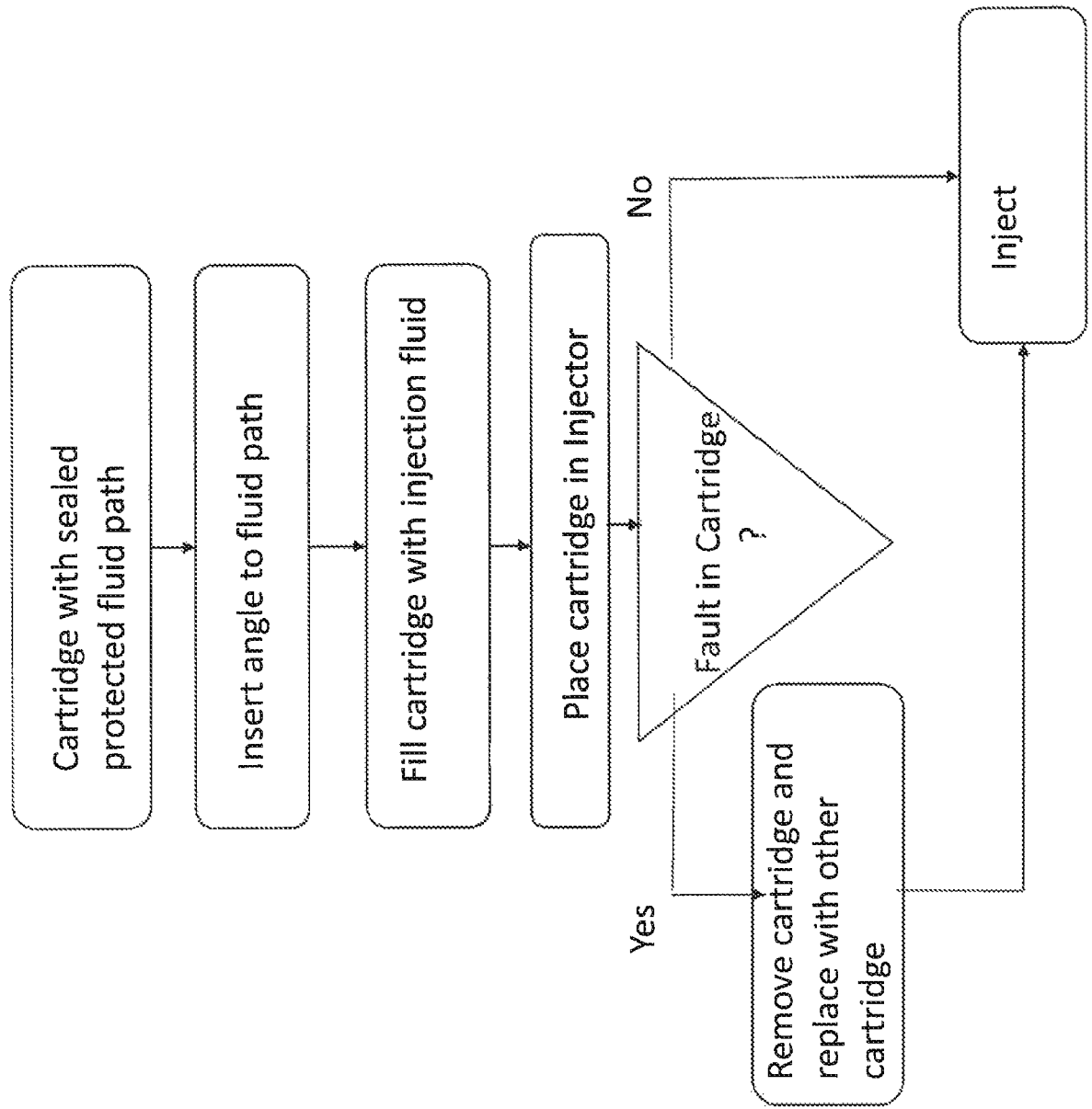
FIG. 21 is a flow chart showing a second cartridge filling and replacing procedure according to an embodiment of the present invention.

Reference is now made to FIG. 21, which illustrates a further method of filling, loading and exchanging a cartridge in accordance with embodiments of the present invention. As discussed, the cartridge is held lengthwise at an angle to the plane of the skin of the patient receiving the injection. In the method, the cartridge with the fluid path is obtained 300 and an angle is made in the fluid path, 302. With the angle in the fluid path the cartridge is filled 304 with injection fluid. Then the cartridge, now sealed to retain sterility, is placed in the injector device 306 and if all goes well and there is no fault 308 then the injector is used by the patient to carry out the injection 310. However if there is a fault in the cartridge, say the use by date has passed and the drug has expired, then the cartridge may be removed 314 and a fresh cartridge inserted.

As discussed above, removal is carried out via an opening in the housing which is opened by removal of a removable cover.

Loading the cartridge into the injector may involve placing the fluid path in mechanical connection with a drive mechanism. The drive mechanism then operates to extend the needle of the fluid path to an injection site under the patient's skin.

The fluid path may be sterile and sealed, and the fluid path is merely in contact with the drive chain or mechanism externally, so that applying and removing the mechanical connection may be carried out while retaining fluid path sterility. The ability to separate the cartridge, which may have biologically active materials, from the rest of the injector means that a more environmentally friendly disposal procedure may be used, as well as allowing for replacement of the cartridge or injector in the event of a fault.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for drug injection comprising:
    a cartridge comprising a reservoir having a lengthwise axis and an injection needle extending from, and formed in one piece with, the reservoir, a portion of the injection needle being bent relative to the lengthwise axis, the reservoir and the injection needle defining a fluid path to carry an injection fluid from the reservoir to a patient at an injection point, the cartridge, including the reservoir, the injection needle and the injection fluid therein, being insertable and removable from the device in a sealed, sterile state; and
    a drive chain mechanically connected to the inserted cartridge, the drive chain comprising a coiled spring and a motion translation unit configured to translate rotary uncoiling of the spring to a lowering motion of the cartridge and needle to move the needle to the injection point, the mechanical connection between the drive chain and the cartridge being external to the fluid path, thereby maintaining the fluid path sterility.

2. The device of claim 1, wherein said fluid path is pre-shaped to contain an angle.

3. The device of claim 1, wherein said drive chain is disconnectable from said fluid path while maintaining said fluid path sterility.

4. The device of claim 1, further comprising a housing and a button to operate said drive chain, the housing being shaped and sized to be held in a one handed grip, the button being positioned to be operated by fingers of said one-handed grip.

5. The device of claim 4, having a front end and a rear end and an adhesive layer for attachment to skin of said patient for said injection.

6. The device of claim 5, the device being attachable and detachable to said patient via said adhesive layer using said one-handed grip and a rolling motion between said front end and said rear end.

7. The device of claim 1, further comprising a cover in said housing, the cover being removable to allow removal of said reservoir via said housing.

8. The device of claim 7, wherein said reservoir is removable with said fluid path.

9. A method for filling, loading and removing a cartridge in an injector device wherein the cartridge is mounted lengthwise in the injector device at an angle to a plane of skin of a patient receiving an injection, the method comprising:
    obtaining a cartridge comprising a reservoir having a lengthwise axis and an injection needle extending from, and formed in one piece with, the reservoir, the reservoir and injection needle defining a fluid path for carrying fluid from the cartridge to an injection site;
    bending the injection needle and forming an angle therein such that said fluid path bends from extending along the lengthwise axis of said reservoir into a direction substantially perpendicular to said plane of the skin;
    filling said cartridge with injection fluid after the forming step;
    loading said cartridge, with said fluid path, into said injector device;
    uncoiling a coiled spring, whereby a motion translation unit translates rotary uncoiling of the spring to a lowering motion of the cartridge and needle to move the needle to an injection point; and
    removing said cartridge from said injector device.

10. The method of claim 9, comprising carrying out said removing upon noticing a fault in said injector device, and placing said cartridge in a second injector device.

11. The method of claim 9, comprising carrying out said removing upon noticing a fault in said reservoir, and placing another cartridge in said injector device.

12. The method of claim 9, comprising providing a housing for said injector device and a removable cover in said housing and opening said removable cover to carry out said loading and said removing.

13. The method of claim 9, wherein said loading step comprises placing said fluid path in mechanical connection with a drive mechanism configured to move the injection needle to an injection site on said patient.

14. The method of claim 13, wherein said fluid path is sterile, and the method further comprising connecting and disconnecting the drive mechanism while retaining said fluid path sterility.

* * * * *